United States Patent
Tanaka et al.

(10) Patent No.: US 6,187,964 B1
(45) Date of Patent: Feb. 13, 2001

(54) METHOD OF PRODUCING PHENOL COMPOUND

(75) Inventors: Kazuo Tanaka, Okayama-ken; Yukio Sakai, Ibaraki-ken; Yasuhiro Shoji, Ibaraki-ken; Takafumi Yoshimura, Ibaraki-ken; Masatoshi Yoshimura, Ibaraki-ken, all of (JP)

(73) Assignee: Mitsubishi Gas Chemical Company, Inc., Tokyo (JP)

( * ) Notice: Under 35 U.S.C. 154(b), the term of this patent shall be extended for 0 days.

(21) Appl. No.: 09/353,311

(22) Filed: Jul. 14, 1999

(30) Foreign Application Priority Data

| | | |
|---|---|---|
| Jul. 17, 1998 | (JP) | 10-203528 |
| May 19, 1999 | (JP) | 11-138533 |
| May 19, 1999 | (JP) | 11-138534 |

(51) Int. Cl.⁷ ................................... C07C 37/00
(52) U.S. Cl. ......................... 568/802; 568/803; 568/806
(58) Field of Search ................... 568/802, 803, 568/806

(56) References Cited

U.S. PATENT DOCUMENTS

| | | | | |
|---|---|---|---|---|
| 3,850,995 | * | 11/1974 | Horlenko | 568/802 |
| 3,875,247 | * | 4/1975 | Bourdin | 568/802 |
| 3,927,122 | * | 12/1975 | Bourdin | 568/802 |
| 3,927,123 | * | 12/1975 | Bourdin | 568/802 |
| 3,962,350 | * | 6/1976 | Horlenko | 568/802 |
| 3,976,702 | * | 8/1976 | Suzuki | 568/802 |
| 4,094,912 | * | 6/1978 | Feinstein | 568/802 |
| 4,465,872 | * | 8/1984 | Suzuki | 568/802 |
| 5,237,092 | | 8/1993 | Tanaka et al. | |
| 5,840,997 | * | 11/1998 | Pannsegrau | 568/802 |

FOREIGN PATENT DOCUMENTS

| | | |
|---|---|---|
| 0520762A2 | 12/1992 | (EP) . |
| 47-27933 | 10/1972 | (JP) . |
| 48-56635 | 8/1973 | (JP) . |
| 1-121229 | 5/1989 | (JP) . |

* cited by examiner

Primary Examiner—Michael L. Shippen
(74) Attorney, Agent, or Firm—Antonelli, Terry, Stout & Kraus, LLP

(57) ABSTRACT

A method of producing a phenol compound comprising a step of oxidizing an aromatic aldehyde to an aryl formate and an aromatic carboxylic acid with an oxygen-containing gas, and a step of decomposing the aryl formate to the phenol compound. To facilitate the separation of the aryl formate and the unreacted aromatic aldehyde, a mixture of the aryl formate and the unreacted aromatic aldehyde is recycled to the oxidation process to concentrate the aryl formate in the oxidation mixture. Alternatively, the oxidation process is carried out in an organic solvent having substantially no ability of dissolving water to increase the conversion of the aromatic aldehyde and the selectivity of the aryl formate, thereby producing the aryl formate in a high yield. In another method, the aryl formate is produced by oxidizing the aromatic aldehyde in the organic solvent having substantially no ability of dissolving water with performic acid generated in situ in the reaction system from the reaction between formic acid and hydrogen peroxide. Since the oxidation proceeds in the organic solvent, hydrogen peroxide in aqueous phase contact the aromatic aldehyde. This significantly reduces the amount of explosive cyclic perther and a high-boiling product.

21 Claims, 1 Drawing Sheet

METHOD OF PRODUCING PHENOL COMPOUND

BACKGROUND OF THE INVENTION

The present invention relates to a method of producing a phenol compound from an aromatic aldehyde. The phenol compound is a very useful compound as a material or intermediate for producing a synthetic resin, an insecticide, an antioxidant, etc.

The phenol compound such as phenol, alkylphenol, etc. has been produced by separation of tar acids or various synthetic methods such as a cymene method. However, a high-purity phenol compound is difficult to obtain by the separation due to small difference in the physical properties between the isomers as well as the homologies. In the synthetic methods, a sulfonation-alkali fusion method is disadvantageous because isomers are by-produced and waste disposal is required. The cymene method requires complicated facilities.

One of other known synthetic method is a method utilizing Baeyer-Villiger reaction, in which the phenol compound is produced through a reaction between the aromatic aldehyde and a peroxide such as peracetic acid, perbenzoic acid, etc. This method is suitable for producing a high-purity phenol compound with less isomers.

Although Baeyer-Villiger reaction generally provides the phenol compound quantitatively in the reaction between an aromatic aldehyde having an electron donative group and a peroxide, provides a large amount of aromatic carboxylic acid with a little phenol compound in the reaction between an aromatic aldehyde having an electron attractive group and an peroxide. Therefore, various proposals have been made to increase the yield of the phenol compound.

For example, Japanese Patent Application Laid-Open No. 47-27933 proposes to quantitatively synthesize the alkylphenol from an aromatic aldehyde using an organic peracid derived from a carboxylic acid showing pKa smaller than 4 in water.

Japanese Patent Application Laid-Open No. 48-56635 proposes a method where the alkylphenol is obtained by a reaction between hydrogen peroxide and an aromatic aldehyde in the presence of an inorganic acid.

However, since performic acid, peracetic acid, hydrogen peroxide, etc. used in these methods are relatively expensive and have danger of explosion, special care has to be made in handling them.

To avoid the danger of direct handling, Japanese Patent Application Laid-Open No. 1-121229 proposes a method of producing a phenol compound, where an aqueous hydrogen peroxide is added to a solution of an aromatic aldehyde in formic acid to form performic acid in situ in the reaction system, and the aromatic aldehyde is oxidized by performic acid to an aryl formate which is then hydrolyzed. However, this method involves the following problems:

(1) Although the method is carried out safely as compared with a method directly utilizing an organic peracid such as performic acid, perbenzoic acid and peracetic acid, a cyclic perether is generated by the reaction between the aromatic aldehyde and hydrogen peroxide. The cyclic perether is in danger of explosion and requires very expensive facilities for safety.

(2) A high-boiling product is produced in the step of forming the aryl formate by the reaction between hydrogen peroxide and a phenol compound formed from a part of the synthesized aryl formate. This reduces the yield of the phenol compound.

Further proposed is a method using another oxidizing agent in place of the peroxide. U.S. Pat. No. 5,237,092 proposes a method where an aromatic aldehyde is oxidized in a water-free condition to an aryl formate and an aromatic carboxylic acid using an oxygen-containing gas as the oxidizing agent. Although this method uses an inexpensive oxidizing agent and is easy to practice, it involves the following problems:

(1) The unreacted aromatic aldehyde and its corresponding aryl formate are hardly separated from each other by distillation due to the extremely small difference between the boiling points. For example, the boiling point of 2,4-dimethylbenzaldehyde is 117° C./25 Torr, while 114° C./25 Torr for 2,4-xylyl formate.

(2) An approach avoiding the above problem is to first completely oxidize the aromatic aldehyde to an aromatic peracid thereby reducing the amount of the unreacted aromatic aldehyde. Thereafter, the aromatic peracid is reacted with freshly supplied aromatic aldehyde to produce the aryl formate and the aromatic carboxylic acid. However, this method requires two-stage reaction and increases the selectivity of the aromatic carboxylic acid with significant decrease in the selectivity of the aryl formate.

SUMMARY OF THE INVENTION

Accordingly, an object of the present invention is to provide a safe and industrially efficient method of producing the phenol compound without using an organic peracid and hydrogen peroxide which are expensive and in danger of explosion.

Another object of the present invention is to provide a method of producing the phenol compound using hydrogen peroxide, which is improved in safety and efficiency.

As a result of intense research on safe and efficient production method of the phenol compound, the inventors have found that the aryl formate and the aromatic carboxylic acid can be advantageously produced, without requiring a solvent in the oxidation of the aromatic aldehyde, by oxidizing the aromatic aldehyde to the aryl formate and the aromatic carboxylic acid with an oxygen-containing gas in a water-free condition, and then separating the aromatic carboxylic acid while recycling a mixture of the aryl formate and the residual aromatic aldehyde difficult to separate by distillation into the oxidation process, thereby concentrating the aryl formate in the reaction liquid from the oxidation process to make the separation of the aryl formate and the residual aromatic aldehyde by distillation easy. The inventors have also found that the phenol compound can be efficiently obtained by decomposing and converting the resulting aryl formate into a corresponding phenol compound, and that an alkali metal compound exhibits a specific catalytic effect in decomposing the aryl formate to efficiently produce the phenol compound.

The inventors have further found that the conversion of the aromatic aldehyde and the selectivity of the aryl formate can be increased without increasing the selectivity of the aromatic carboxylic acid to thereby produce the aryl formate in a high yield, i.e., produce the phenol compound efficiently when the oxidation of the aromatic aldehyde with the oxygen-containing gas is carried out in an organic solvent having substantially no ability of dissolving water.

In addition, the inventors have made intense research on the methods of producing the phenol compound from the aromatic aldehyde using hydrogen peroxide. As a result thereof, the inventors have found that the amounts of the cyclic perether and the high-boiling product in the synthesis of the aryl formate by the reaction between the aromatic aldehyde having at least one substituent group on the aromatic ring, formic acid and the aqueous hydrogen peroxide can be significantly reduced by using an organic solvent having substantially no ability of dissolving water, thereby improving the yield of the phenol compound and the safety of the production method.

The present invention has been achieved by these findings.

Thus, in a first aspect of the present invention, there is provided a method of producing a phenol compound comprising a first step of producing an aryl formate and an aromatic carboxylic acid by oxidizing an aromatic aldehyde with an oxygen-containing gas to form a reaction product; a second step of separating the aromatic carboxylic acid, a mixture of the aryl formate and an unreacted aromatic aldehyde and the aryl formate from the reaction product obtained in the first step; and a third step of decomposing the aryl formate to the phenol compound; the mixture of aryl formate and the unreacted aromatic aldehyde separated in the second step being recycled to the first step.

In a second aspect of the present invention, there is provided a method of producing an aryl formate and an aromatic carboxylic acid comprising a first step of producing an aryl formate and an aromatic carboxylic acid by oxidizing an aromatic aldehyde with an oxygen-containing gas to form a reaction product at 10–120° C. in the absence of solvent; and a second step of separating the aromatic carboxylic acid, a mixture of the aryl formate and an unreacted aromatic aldehyde and the aryl formate from the reaction product obtained in the first step; the mixture of aryl formate and the unreacted aromatic aldehyde separated in the second step being recycled to the first step.

In a third aspect of the present invention, there is provided a method of producing a phenol compound, comprising a first step of producing an aryl formate and an aromatic carboxylic acid by oxidizing an aromatic aldehyde with an oxygen-containing gas in an organic solvent having substantially no ability of dissolving water to form a reaction product; and a second step of decomposing the aryl formate obtained in the first step to the phenol compound.

In a fourth aspect of the present invention, there is provided a method of producing an aryl formate and an aromatic carboxylic acid, comprising a step of oxidizing an aromatic aldehyde to the aryl formate and the aromatic carboxylic acid with an oxygen-containing gas in an organic solvent having substantially no ability of dissolving water to form a reaction product.

In a fifth aspect of the present invention, there is provided a method of producing an phenol compound, comprising a fist step of reacting an aromatic aldehyde having at least one substituent group, formic acid and an aqueous hydrogen peroxide in the presence of an organic solvent having substantially no ability of dissolving water to thereby produce an aryl formate; and a second step of hydrolyzing the aryl formate obtained in the first step to the phenol compound.

DETAILED DESCRIPTION OF THE INVENTION

Figure 1:
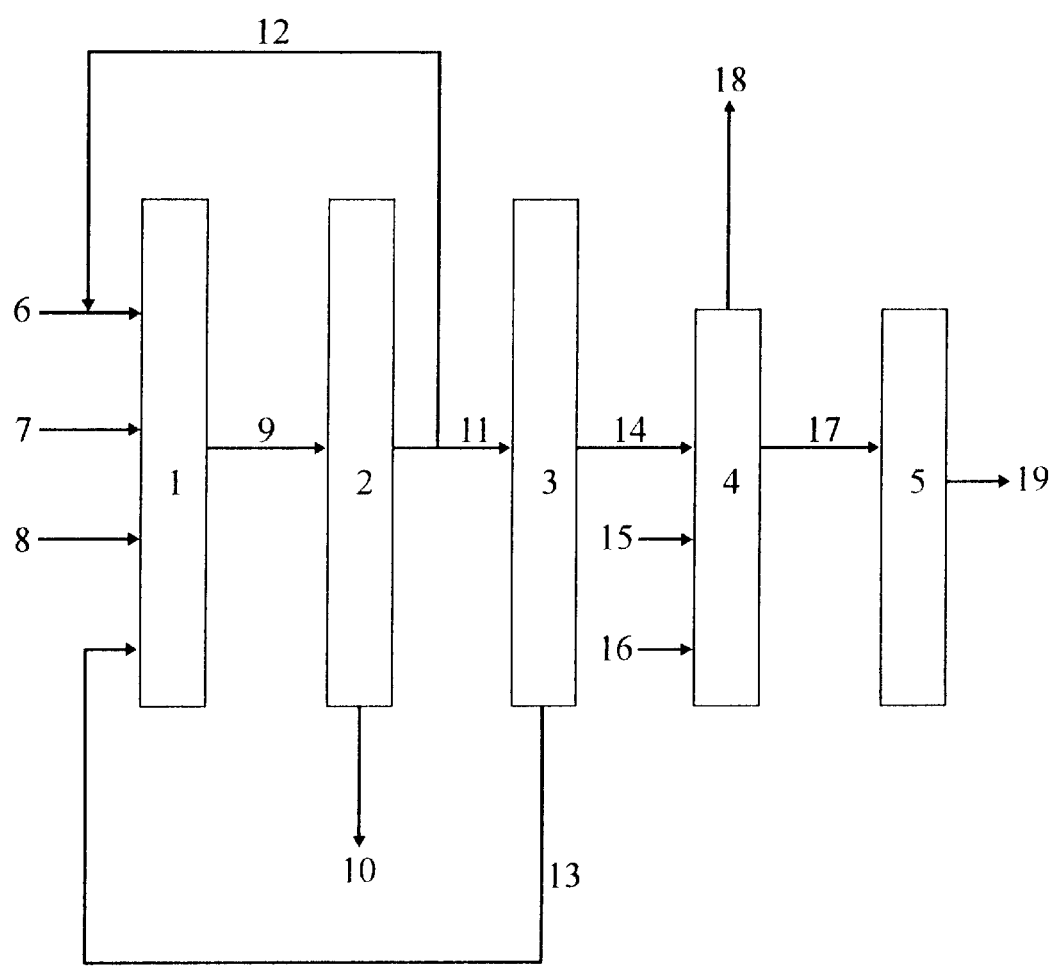
FIG. 1 is a flow chart showing one embodiment of producing the phenol compound according to the present invention.

[1] First Production Method
(i) First Step

The starting aromatic aldehyde usable in the first production method may include benzaldehyde which may have on the aromatic ring at least one substituent group such as alkyl, cycloalkyl, aryl, alkoxy, aryloxy, hydroxy, etc. Specific examples of the aromatic aldehyde may be o-, m- or p-tolualdehyde, 2,4-dimethylbenzaldehyde, 2,5-dimethylbenzaldehyde, 3,4-dimethylbenzaldehyde, p-ethylbenzaldehyde, p-methoxybenzaldehyde, p-cuminaldehyde, biphenylaldehyde, n-butylbenzaldehyde, p-phenoxybenzaldehyde, p-hydroxybenzaldehyde, p-cyclohexylbenzaldehyde, 2,4,5-trimethylbenzaldehyde, 2,4,6-trimethylbenzaldehyde, 2,3,4-trimethylbenzaldehyde, etc. Particularly, the isomers of dimethylbenzaldehyde and 2,4,5-trimethylbenzaldehyde are preferably used because they are industrially mass-produced.

In the first step, the aromatic aldehyde is oxidized to the aryl formate and the aromatic carboxylic acid using an oxygen-containing gas as the oxidizing agent. The oxygen-containing gas may be pure oxygen, air, air with concentrated oxygen, or a mixed gas of oxygen and an inert gas such as carbon dioxide, nitrogen, etc. Air is generally used.

The reaction temperature of the first step is generally –20 to 150° C., preferably 10 to 120° C. When the reaction temperature is too low, the reaction rate is low, whereas the selectivity of the aryl formate is decreased when the reaction temperature is too high. The reaction pressure is generally from atmospheric pressure to 60 kg/cm$^2$G, preferably from atmospheric pressure to 50 kg/cm$^2$G. Since a high oxygen partial pressure increases the reaction rate to result in a high yield production of the aryl formate, and the loss of the resultant liquid associated with off-gas is avoided, the first step is preferably carried out under pressure. However, since a pressure exceeding 60 kg/cm$^2$G produces no further effect, the first step is generally carried out in the above pressure range.

Although the use of a catalyst is not critical, the first step of synthesizing the aryl formate is preferably carried out in the presence of a metal catalyst such as cobalt, manganese, iron, platinum, palladium, vanadium, ruthenium, zirconium, aluminum, antimony, beryllium and copper. A cobalt catalyst is particularly preferable. The metal catalyst is used in an amount of 0.001 to 50 ppm, preferably 0.01 to 10 ppm based on the total amount of the reaction liquid. When the amount is less than 0.001 ppm, the reaction rate is low. An amount exceeding 50 ppm decreases the selectivity of the aryl formate.

The conversion of the aromatic aldehyde in the first step is 5 to 85 mol %, preferably 7 to 70 mol %. A conversion exceeding 85 mol % increases the selectivity of the aromatic carboxylic acid to result in a decreased selectivity of the aryl formate. On the other hand, although a conversion less than 5 mol % increases the selectivity of the aryl formate, the amount of the unreacted starting aromatic aldehyde is unfavorably increased.

(ii) Second Step

The reaction mixture obtained in the first step contains the unreacted aromatic aldehyde, the aryl formate, the aromatic carboxylic acid and a slight amount of impurities. In the second step, the aromatic carboxylic acid, a mixture of the aryl formate and the unreacted aromatic aldehyde, and the aryl formate are separated from the reaction mixture usually by distillation.

However, the aromatic aldehyde and the aryl formate are very difficult to separate from each other by distillation due to extremely small difference between their boiling points. Therefore, in the second step, the high-boiling aromatic carboxylic acid is first separated from the reaction liquid in a first distillation column. The separated aromatic carboxylic acid may be used as a starting material or intermediate material for producing various industrial chemicals.

After the separation of the aromatic carboxylic acid from the reaction liquid by distillation in a first distillation column, a mixture of the unreacted aromatic aldehyde and the aryl formate is obtained. The important feature of the first production method resides in that at least a part of the mixture of the aryl formate and the unreacted aromatic aldehyde separated in the second step is recycled to the first step. Since the recycled aryl formate and aromatic aldehyde serve as a solvent, the first step of aryl formate synthesis requires no specific solvent. With such a recycling, the mixture of the aryl formate and the aromatic aldehyde difficult to separate can be effectively reused, and the aryl formate is concentrated in the reaction liquid in the first step. Therefore, since the separation of the aryl formate and the residual aromatic aldehyde in the second step is facilitated and the additional step of separating the solvent is avoided, the aryl formate and the phenol compound can be industrially produced to extreme advantage.

The rest of the mixture of the aromatic aldehyde and the aryl formate is supplied to a second distillation column, where the unreacted aromatic aldehyde is separated and recycled to the first step. The concentration of the aryl formate in the mixture being supplied to the second distillation column is 40 weight % or more, preferably 60 weight % or more. The concentration of the aryl formate in the effluent liquid from the top of the second distillation column is 90 weight % or more, preferably 95 weight % or more. The separated aryl formate, also usable as a material for producing products of various purposes, is decomposed to the phenol compound in the third step.

(iii) Third Step

In the third step, the aryl formate is decomposed to the phenol compound by the following methods:
(1) a thermal decomposition to the phenol compound and carbon monoxide;
(2) a hydrolysis to the phenol compound and formic acid;
(3) an alkaline decomposition to the phenol compound and a salt of formic acid; and
(4) a methanolysis to the phenol compound and methyl formate.

The thermal decomposition (1) of the aryl formate to the phenol compound and carbon monoxide is efficiently carried out by thermally decomposing the aryl formate while contacting it with an alkali metal compound.

The alkali metal compound used as a catalyst in the thermal decomposition may include sodium hydroxide, potassium hydroxide, sodium carbonate, potassium carbonate, sodium bicarbonate, potassium bicarbonate, sodium chloride, potassium chloride, sodium bromide, potassium bromide, sodium iodide, potassium iodide, sodium formate, potassium formate, a sodium alkylbenzoate, a potassium alkylbenzoate, sodium methlate, potassium methylate, a sodium alkylphenolate, a potassium alkylphenolate, etc. Of the above compounds, sodium hydroxide, potassium hydroxide, potassium carbonate, the sodium alkylphenolate, the potassium alkylphenolate, potassium chloride, sodium formate and potassium formate are preferably used. Activated carbon carrying the alkali metal compound is also usable.

The thermal decomposition may be carried out by a liquid phase reaction such as a liquid-phase homogeneous catalytic reaction, a liquid-phase suspended catalytic reaction, a fixed bed liquid-phase reaction, etc. or a fixed bed vapor-phase reaction. The liquid-phase reaction is preferable. In the liquid-phase catalytic reaction, the alkali metal compound is used in an amount of 0.01 to 30 weight %, preferably 0.05 to 25 weight % based on the amount of the aryl formate.

The temperature of the thermal decomposition is 110 to 350° C., preferably 150 to 330° C. The aryl formate begins to decompose at about 90° C. Although the thermal decomposition takes place more rapidly with increasing thermal decomposition temperature, the side reaction becomes significant at a temperature higher than 350° C. The reaction pressure is generally in the range of atmospheric pressure to 2 MPa, and suitably adjusted so that the aryl formate is kept in liquid state at the thermal decomposition temperature. The residence time is 0.01 to 5 hours, preferably 0.1 to 2 hours. A longer residence time detrimentally causes the side reaction.

The aryl formate is nearly quantitatively decomposed to the phenol compound and carbon monoxide. The gaseous carbon monoxide enters into vapor phase, while the phenol compond remains in liquid phase. After removing the suspended catalyst from the liquid phase by a usual method or distilling the liquid phase when the catalyst is dissolved therein, a purified phenol compound is obtained.

The hydrolysis (2) of the aryl formate to the phenol compound and formic acid is carried out by contacting the aryl formate with water.

The molar ratio of water to the aryl formate is 1.0 to 100, preferably 1.5 to 10. When the molar ratio is less than 1.0, the aryl formate becomes included in the phenol compound. When the molar ratio exceeds 100, the concentration of the phenol compound and formic acid in the resultant mixture are too small to require a high heat energy for recovering it.

The temperature for hydrolysis is 60 to 300° C., preferably 100 to 280° C. Although the rate of hydrolysis increases with increasing temperature, an excessively high temperature unfavorably causes the decomposition of the resultant phenol compound. The residence time of hydrolysis is 0.1 to 10 hours, preferably 0.2 to 5 hours. Since the hydrolysis is a reaction between an oil phase and a water phase, a sufficient stirring is required. The reaction pressure is selected from a range of atmospheric pressure to 10 MPa so that the reaction liquid is kept in liquid state.

The aryl formate is hydrolyzed to the phenol compound and formic acid, and the formic acid is distributed to the water phase and the phenol compound is distributed to the oil phase. These products may be separated by oil-water separation or distillation.

The alkaline decomposition (3), the aryl formate is efficiently decomposed to the phenol compound and a salt of formic acid by contacting it with an aqueous alkali solution.

The catalyst for the alkaline decomposition may be sodium hydroxide, potassium hydroxide, sodium carbonate, potassium carbonate, sodium hydrogencarbonate, potassium hydrogencarbonate, etc.

In the alkaline decomposition using sodium hydroxide or potassium hydroxide as the catalyst, the molar ratio of the alkali to the aryl formate is 1.0 to 1.1. The use of an excessive amount is not preferable because the phenol compound is further converted to a phenolate. The concentration of sodium hydroxide or potassium hydroxide in an aqueous solution is usually 5 to 50% by weight. The alkaline decomposition temperature and the residence time are not specifically limited in this method, and the aryl formate is momentarily decomposed to the phenol compound and the salt of formic acid even when mixed with the aqueous solution of alkali at room temperature.

In the alkaline decomposition using sodium carbonate, potassium carbonate, sodium hydrogencarbonate or potassium hydrogencarbonate as the catalyst, the molar ratio of the alkali to the aryl formate is 0.1 or more and preferably up to 10. In this method, the use of an excessive amount does not convert the phenol compound to a phenolate. The concentration of sodium carbonate, potassium carbonate, sodium hydrogencarbonate or potassium hydrogencarbonate in aqueous solution is usually 5 to 30% by weight.

By the methanolysis (4), the aryl formate is converted to the phenol compound and methyl formate. The methanolysis is carried out using methanol in excess, and the molar ratio of methanol to the aryl formate is preferably 1.5 to 20. The reaction temperature is 50 to 250° C. Known catalyst for ester interchange reaction may be used in this method. The pressure is regulated so that the reaction liquid is kept in liquid state at a given reaction temperature.

The above steps (i), (ii) and (iii) may be carried out either batch-wisely or continuously, preferably continuously.

Next, the present invention is described with reference to the drawings. FIG. 1 is a flow chart showing one embodiment of producing the phenol compound by the method of the present invention. As shown in FIG. 1, into an oxidation reactor 1 for the first step, is introduced the starting aromatic aldehyde from a flow path 6, is introduced a mixture of the aryl formate and the aromatic aldehyde from a flow path 12, and is introduced a recovered aromatic aldehyde from a flow path 13. The oxygen-containing gas is introduced from a flow path 7 and the catalyst is introduced from a flow path 8 to thereby cause the oxidation of the aromatic aldehyde. The oxidation mixture from the oxidation reactor 1 is supplied to a first distillation column 2 through a flow path 9. In the first distillation column 2, the aromatic carboxylic acid is removed through a flow path 10. Part of a top effluent from the first distillation column 2 is recycled to the oxidation reactor 1 through a flow path 12. The rest of the top effluent from the first distillation column 2 is supplied to a second distillation column 3 through a flow path 11. The aryl formate from the top of the second distillation column 3 is supplied to a decomposition reactor 4 through a flow path 14. In the method (1) of thermal decomposition to the phenol compound and carbon monoxide, the alkali metal compound as the catalyst is introduced to the decomposition reactor 4 from a flow path 15 and carbon monoxide is removed from a flow path 18. In the method (2) of hydrolysis to the phenol compound and formic acid, water is introduced from a flow path 16 and formic acid is separated from the flow path 18. In the method (3) of alkaline decomposition to the phenol compound and the salt of formic acid, an aqueous solution of alkali is introduced from the flow path 15, and the salt of formic acid is separated from the flow path 18. In the method (4) of methanolysis to the phenol compound and methyl formate, methanol is introduced from the flow path 16 and methyl formate is separated from the flow path 18. In any methods, the phenol compound is recovered from a flow path 17 and supplied to a distillation column 5 for purification. The purified phenol compound is obtained from a flow path 19.

[2] Second Production Method
(i) First Step

In the second production method, the same starting aromatic aldehyde as usable in the first production method may be used. Particularly, benzaldehyde, tolualdehyde, dimethylbenzaldehyde and trimethylbenzaldehyde are preferably used.

In the second production method, the aryl formate is produced by oxidizing the aromatic aldehyde with the oxygen-containing gas in the organic solvent having substantially no ability of dissolving water. Although the oxidation may be carried out in the absence of a catalyst, it is preferred to use the same catalyst as used in the first step of the first production method in an amount as specified in the first production method. Also, the same oxygen-containing gas as used in the first production method may be used in this method.

The reaction temperature is generally 10 to 150° C. A reaction temperature exceeding 150° C. decreases the selectivity of the aryl formate, while a reaction temperature lower than 10° C. significantly decreases the reaction rate to result in a poor productivity. The reaction pressure is generally from atmospheric pressure to 6 MPa. The reaction rate increases with increasing oxygen partial pressure to result in an increased yield of the aryl formate.

The solvent used in the oxidation step is an organic solvent having substantially no ability of dissolving water. Examples of the organic solvent include an aliphatic hydrocarbon such as hexane and heptane, an aromatic hydrocarbon such as benzene, toluene, xylene and pseudocumene, an alkyl halide such as methyl chloride and an alkylene halide such as methylene chloride. The aromatic hydrocarbon is preferable due to its good compatibility with the starting material and the product. The weight ratio of the organic solvent to the aromatic aldehyde is preferably 20:1 to 1:1.

With the use of the organic solvent having substantially no ability of dissolving water, the conversion of the aromatic aldehyde can be increased as high as 85 mol % or more without increasing the selectivity of the aromatic carboxylic acid to thereby obtain the aryl formate in a high yield. Namely, the amount of the unreacted aromatic aldehyde, which is very difficult to be separated from the aryl formate by distillation, can be significantly reduced. Therefore, the aryl formate can be easily separated from the reaction mixture.

(ii) Second Step

The aryl formate obtained in the manner mentioned above may be converted to the corresponding phenol compound by any of the methods (1) to (4) described above. The method of hydrolysis or thermal decomposition is particularly preferable.

[3] Third Production Method
(i) First Step

In the third production method, usable as the starting material is an aromatic aldehyde having on the aromatic ring at least one substituent group such as alky, cycloalkyl, aryl, alkoxy, aryloxy, hydroxy, etc. Specific examples of the starting aromatic aldehyde may be tolualdehyde, dimethylbenzaldehyde, trimethylbenzaldehyde, ethylbenzaldehyde, methoxybenzaldehyde, cuminaldehyde, biphenylaldehyde, butylbenzaldehyde, phenoxybenzaldehyde, hydroxybenzaldehyde, cyclohexylbenzaldehyde, etc. Particularly, tolualdehyde, dimethylbenzaldehyde and trimethylbenzaldehyde are preferably used. The aryl formate is produced by oxidizing the aromatic aldehyde in an organic solvent having substantially no ability of dissolving water with performic acid generated by the reaction between formic acid and hydrogen peroxide in aqueous solution. The organic solvent having substantially no ability of dissolving water is the same as those used in the second production method.

With the use of the organic solvent having substantially no ability of dissolving water, the aromatic aldehyde is dissolved in the organic solvent, while formic acid and hydrogen peroxide is present in aqueous phase. The performic acid generated by the reaction between hydrogen peroxide and formic acid in aqueous phase transfers into the organic solvent, reacting there with the aromatic aldehyde to produce the aryl formate. Thus, the direct reaction between the aromatic aldehyde in the organic solvent and hydrogen peroxide in aqueous phase is avoided to thereby prevent the formation of the cyclic perether. Also, since the resultant aryl formate is in the organic solvent and hardly subjected to hydrolysis, the phenol compound is scarcely produced during the oxidation step. Even when the phenol compound is produced, the high-boiling product is not produced because the phenol compound is in the organic solvent and does not react with hydrogen peroxide in aqueous phase.

The concentration of formic acid in the reaction liquid of the first step is preferably 70% by weight or more. A concentration lower than 70% by weight reduces the reaction rate to thereby result in poor productivity. The molar ratio of formic acid to the aromatic aldehyde is 2 to 5. The reaction rate is reduced when the molar ratio is less than 2. A molar ratio larger than 5 shows no increase in the reaction rate.

The concentration of hydrogen peroxide in the aqueous hydrogen peroxide is 30% by weight or more. A concentration lower than 30% by weight reduces the reaction rate to thereby result in poor productivity. The molar ratio of hydrogen peroxide to the aromatic aldehyde is 0.9 to 1.5. When less than 0.9, the conversion of the aromatic aldehyde is reduced to make the recovery of the starting material energy-consuming, while the amount of the high-boiling product increases when exceeding 1.5.

The weight ratio of the organic solvent to the aromatic aldehyde is 3 or more. A ratio lower than 3 increases the contact of the aromatic aldehyde with hydrogen peroxide to result in the production of the cyclic perether and the high-boiling product in large amount.

The reaction temperature is 30 to 100° C. When exceeding 100° C., hydrogen peroxide decomposes vigorously. The reaction rate is significantly slow when less than 30° C. to result in a poor productivity.

(ii) Second Step

After the first step, the aryl formate is separated from the reaction liquid by distillation, etc., and converted to the corresponding phenol compound in the same manner as in the third step of the first production method. Since the reaction liquid includes water, the reaction liquid may be subjected to the hydrolysis (2) mentioned above without separating the aryl formate.

The present invention will be explained in more detail by reference to the following example which should not be construed to limit the scope of the present invention.

In the following examples and comparative examples, "%" is by mole and "ppm" is by weight unless otherwise indicated.

The conversion and the selectivity were respectively calculated from the following formulae:

Conversion=(reacted amount of starting material (mol)/supplied amount of starting material (mol))×100%, and Selectivity=(produced amount (mol)/(reacted amount of starting material (mol))×100%.

EXAMPLE 1

First Step

Into a 6-liter circulating autoclave equipped with a stirrer, was charged 3000 g of 2,4-dimethylbenzaldehyde containing cobalt naphthenate in an amount of 0.03 ppm in terms of cobalt. Then, air was introduced thereto to proceed the oxidation at a reaction temperature of 60° C. for 45 minutes at an off-gas oxygen concentration of 10 volume % under a pressure of 25 g/cm²G.

The analysis of the oxidation liquid showed that the conversion of the aldehyde was 31%, the selectivity of 2,4-dimethylbenzoic acid was 58%, and the selectivity of 2,4-xylyl formate was 41%.

Recycling 1

A mixture of the unreacted 2,4-dimethylbenzaldehyde and 2,4-xylyl formate were obtained by distilling off 2,4-dimethylbenzoic acid from the reaction liquid obtained in the first step. The obtained mixture consisted of 82% by weight 2,4-dimethylbenzaldehyde and 18% by weight 2,4-xylyl formate. The mixture was subjected to oxidation reaction at 70° C. in the same manner as in the first step. The analysis of the oxidation liquid showed that the conversion of the aldehyde was 36%, the selectivity of 2,4-dimethylbenzoic acid was 58%, and the selectivity of 2,4-xylyl formate was 41%.

Recycling 2

Another portion of the liquid obtained in the first step was distilled to remove 2,4-dimethylbenzoic acid, thereby obtaining a mixture of the unreacted 2,4-dimetylbenzaldehyde and 2,4-xylyl formate. The obtained mixture contained 62% by weight 2,4-dimethylbenzaldehyde and 37% by weight 2,4-xylyl formate. The mixture was subjected to oxidation reaction at 75° C. in the same manner as in the first step. The analysis of the oxidation liquid showed that the conversion of the aldehyde was 45%, the selectivity of 2,4-dimethylbenzoic acid was 58%, and the selectivity of 2,4-xylyl formate was 41%.

Second Step

The liquid obtained in the first step was distilled in a first distillation column to remove 2,4-dimethylbenzoic acid, thereby recovering a mixture of the unreacted 2,4-dimetylbenzaldehyde and 2,4-xylyl formate. The obtained mixture contained 40.8% by weight 2,4-dimethylbenzaldehyde and 59.0% by weight 2,4-xylyl formate.

The effluent from the first distillation column was subjected to batch-distillation in a second distillation column with 40 theoretical stages under 25 Torr. The effluent from the second distillation column contained 93.0% by weight of 2,4-xylyl formate and 7.0% by weight of 2,4-dimethylbenzaldehyde, showing that the distillation efficiency of 2,4-xylyl formate was 86.0%. The 2,4-xylyl formate thus obtained had a purity of 93.0% by weight and was used as the starting material in the following third step.

Third Step

A coiled tube with a length of 4 m and an inter diameter of 6 mm was disposed in a heat medium tank of 260° C. A mixture comprising 98 parts of liquid 2,4-xylyl formate with a purity of 93.0% by weight obtained in the second step and 2 parts of 2,4-xylenol containing potassium salt of 2,4-xylenol in an amount of 0.77% by weight based on 2,4-xylyl formate was continuously passed through the coiled tube under pressure of 0.5 MPa over 5 hours. The reaction mixture was cooled to room temperature at the outlet of the coiled tube to effect the vapor-liquid separation. The result of the quantitative gas chromatographic analysis on the obtained liquid showed that the conversion of 2,4-xylyl formate was 100% and the selectivity of 2,4-xylenol was 99%. The result of the quantitative gas chromatographic analysis showed that the obtained gas contained 99.75% of carbon monoxide, 0.25% of carbon dioxide and 6 ppm of organic gas such as methane, etc.

EXAMPLES 2 TO 5 AND COMPARATIVE EXAMPLE 1

Into a reactor equipped with a stirrer, were added 2,4-xylyl formate with a purity of 93.0% by weight obtained in Example 1 and various alkali metal compounds. Then, the contents were heated to 200° C. while purging the evolved carbon monoxide for one hour. The resultant mixture was quantitatively analyzed by gas chromatography. The alkali metal compounds, the addition ratio thereof to 2,4-xylyl formate and the reaction results are shown in Table 1.

TABLE 1

|  | Alkali metal compound | Addition ratio (%) | Conversion (%) | Selectivity (%) |
|---|---|---|---|---|
| Example 2 | Sodium hydroxide | 8 | 99.2 | 100 |
| Example 3 | Potassium hydroxide | 15 | 100 | 99 |
| Example 4 | Potassium carbonate | 2 | 80.5 | 100 |
| Example 5 | Potassium chloride | 1 | 32.0 | 100 |
| Comparative Example 1 | None | — | 9.2 | 100 |

EXAMPLE 6

Into a SUS pressure vessel equipped with a stirrer, were charged 82 parts of 2,4-xylyl formate with a purity of 93.0% by weight obtained in Example 1 and 18 parts of water. The contents were kept at 175° C. for one hour in nitrogen atmosphere, and then the oil layer of the reaction liquid was quantitatively analyzed by gas chromatography. The conversion of 2,4-xylyl formate was 100% and the selectivity of 2,4-xylenol was 98%.

EXAMPLE 7

Into a SUS pressure vessel equipped with a stirrer, were charged 30 parts of 2,4-xylyl formate with a purity of 93.0% by weight obtained in Example 1 and 70 parts of methanol. The contents were kept at 150° C. for one hour in nitrogen atmosphere, and then the reaction liquid was quantitatively analyzed by gas chromatography. The conversion of 2,4-xylyl form ate was 86% and the selectivity of 2,4-xylenol was 98%.

EXAMPLE 8

Into a SUS pressure vessel equipped with a stirrer, were charged 35 parts of 2,4-xylyl formate with a purity of 93.0% by weight obtained in Example 1 and 65 parts of 10% by weight aqueous solution of sodium hydrogencarbonate. The contents were kept at 100° C. for one hour in nitrogen atmosphere, and then the oil phase was quantitatively analyzed by gas chromatography. The conversion of 2,4-xylyl formate was 84% and the selectivity of 2,4-xylenol was 98%.

EXAMPLE 9

Into a SUS pressure vessel equipped with a stirrer, were charged 49 parts of 2,4-xylyl formate with a purity of 93.0% by weight obtained in Example 1 and 51 parts of 24% by weight aqueous solution of sodium hydroxide. The contents were mixed at room temperature in nitrogen atmosphere and liquid-liquid separated. The oil phase was quantitatively analyzed by gas chromatography. The conversion of 2,4-xylyl formate was 100% and the selectivity of 2,4-xylenol was 100%.

EXAMPLE 10

The same procedures as in Example 1 were repeated except for using 2,4,5-trimethylbenzaldehyde in place of 2,4-dimethylbenzaldehyde. The results of analysis on the reaction liquid showed that the conversion of the aldehyde was 32%, the selectivity of 2,4,5-trimethylbenzoic acid was 57%, and the selectivity of 2,4,5-tirmethylphenyl formate was 42%.

EXAMPLE 11

Into a 0.5-liter circulating autoclave equipped with a stirrer, were charged 20 g of 2,5-dimethylbenzaldehyde and 180 g of benzene. To the solution, an amount of cobalt naphthenate was added as the catalyst so that the cobalt concentration is 0.1 ppm. Then, air was introduced thereto to proceed the oxidation at a reaction temperature of 40° C. for 3 hours under a reaction pressure of 1 MPa. The analysis of the reaction liquid showed that the conversion of the aldehyde was 99 mol %, the selectivity of 2,5-xylyl formate was 42%, and the selectivity of 2,5-dimethylbenzoic acid was 58%. From the reaction liquid, 2,5-xylenol formate was separated by distillation.

After adding potassium salt of xylenol in an amount of 0.47 weight % based on the separated 2,5-xylyl formate, the thermal decomposition was carried out at 200° C. for one hour to obtain 2,5-xylenol in 41% yield.

EXAMPLE 12

A reaction liquid obtained in the same manner as in Example 11 was added with 20 g of water and subjected to hydrolysis for 3 hours after raised to 100° C. 2,5-Xylenol was obtained in 41% yield.

COMPARATIVE EXAMPLE 2

The same procedures of Example 11 were repeated except for replacing the whole amount of benzene with the aldehyde. The conversion of 2,5-dimethylbenzaldehyde was 90 mol %. The selectivity was 20% for 2,5-xylyl formate, 70% for 2,5-dimethylbenzoic acid, and 10% for p-xylene.

As a result of thermal decomposition in the same manner as in Example 11, 2,5-xylenol was obtained in 18% yield. As compared with Example 11 using benzene as the solvent, the selectivity of the aryl formate was low and p-xylene was by-produced.

EXAMPLE 13

Into a 200 ml flask equipped with a stirrer and a reflux condenser, were charged 14 g of formic acid of 70% by weight concentration, 45 g of benzene and 10 g of 2,5-dimethylbenzaldehyde. After heating the contents to 60° C., 4 g of aqueous hydrogen peroxide were added dropwise over 20 minutes. The reaction was completed after 40 minutes of the addition. The conversion of 2,5-dimethylbenzaldehyde was 90 mol %. The respective selectivity was 94% for 2,5-xylyl formate and 2,5-xylenol, 5% for 2,5-dimethylbenzoic acid, 0.1% for the cyclic perether, and 0.9% for the high-boiling product.

After adding 30 g of water, the reaction liquid was heated to 100° C. and subjected to hydrolysis for 3 hours to obtain 2,5-xylenol in a yield of 83 mol %.

COMPARATIVE EXAMPLE 3

The procedures of Example 13 were repeated except for omitting the use of benzene. Likewise Example 13, the conversion of 2,5-dimethylbenzaldehyde was 90 mol %. The respective selectivity was 83% for 2,5-xylyl formate and 2,5-xylenol, 4% for 2,5-dimethylbenzoic acid, 3% for the cyclic perether, and 10% for the high-boiling product. The reaction liquid was hydrolyzed in the same manner as in Example 13 to obtain 2,5-xylenol in a yield of 72 mol %.

Upon comparing Example 13 using benzene as the organic solvent, it was found that the cyclic perether and the high-boiling product were produced in larger amounts.

As described above, in the first production method, the aromatic aldehyde is oxidized by the oxygen-containing gas to the aryl formate and the aromatic carboxylic acid, and then, the aromatic carboxylic acid, a mixture of the aryl formate and the aromatic aldehyde and the aryl formate are separated from the obtained reaction mixture. The separated mixture of the aryl formate and the aromatic aldehyde is recycled to the oxidation reactor to thereby produce the aryl formate and the aromatic carboxylic acid. With such a recycling, the aryl formate is concentrated in the oxidation mixture to make the separation of the aryl formate from the unreacted aromatic aldehyde easier. The separated aryl formate is decomposed to produce the corresponding phenol compound in a high yield. Since the use of expensive and explosive organic peracid and hydrogen peroxide can be avoided, this production method provides a safe and industrially advantageous method of producing phenol compound. In addition, since the by-products such as aromatic carboxylic acid, carbon monoxide and formic acid derivative produced in this method are also industrially useful, the present invention is industrially quite advantageous.

In the second production method, the aromatic aldehyde is oxidized to the aryl formate by the oxygen-containing gas in the organic solvent having substantially no ability of dissolving water. Since the conversion of the aromatic aldehyde and the selectivity of the aryl formate are increased without increasing the selectivity of the aromatic carboxylic acid, the phenol compound can be obtained in a high yield. Also, since the explosive peracids are not used, the phenol compound is produced safely and efficiently.

In the third production method, the aromatic aldehyde is oxidized in the organic solvent having substantially no ability of dissolving water with performic acid generated in situ in the reaction system from the reaction between formic acid and hydrogen peroxide. Since the aromatic aldehyde is present in the organic solvent while hydrogen peroxide in aqueous layer, the contact between the aromatic aldehyde and hydrogen peroxide can be avoided, this prventing the formation of the explosive cyclic perether and the high-boiling product to thereby produce the aryl formate in a high yield. By hydrolyzing the obtained aryl formate, the corresponding phenol compound can be easily produced. Since the amount of the explosive cyclic perether and the high-boiling product is small and the recovered formic acid can be reused in the production method, the third production method provides a safe and advantageous method of producing the phenol compound form the aromatic aldehyde.

What is claimed is:

1. A method of producing a phenol compound comprising:
   a first step of producing an aryl formate and an aromatic carboxylic acid by oxidizing an aromatic aldehyde with an oxygen-containing gas to form a reaction product;
   a second step of separating the aromatic carboxylic acid, a mixture of the aryl formate and an unreacted aromatic aldehyde and the aryl formate from the reaction product obtained in the first step; and
   a third step of decomposing the aryl formate to the phenol compound;
   the mixture of aryl formate and the unreacted aromatic aldehyde separated in the second step being recycled to the first step.

2. The method according to claim 1, wherein the first step is carried out at −20 to 150° C. in the absence of solvent.

3. The method according to claim 1, wherein the third step is carried out by thermally decomposing the aryl formate to the phenol compound and carbon monoxide at 110 to 350° C. in liquid phase in the presence of an alkali metal compound.

4. The method according to claim 3, wherein the alkali metal compound is at least one compound selected from the group consisting of sodium hydroxide, potassium hydroxide, potassium carbonate, sodium alkylphenolates, potassium alkylphenolates, potassium chloride, sodium formate and potassium formate.

5. The method according to claim 1, wherein the third step is carried out by hydrolyzing the aryl formate to the phenol compound and formic acid at 60 to 300° C.

6. The method according to claim 1, wherein the third step is carried out by decomposing the aryl formate to the phenol compound and an alkali salt of formic acid by an aqueous solution of alkali.

7. The method according to claim 1, wherein the third step is carried out by decomposing the aryl formate to the phenol composition and methyl formate by methanol at 50 to 250° C.

8. A method of producing an aryl formate and an aromatic carboxylic acid comprising:
   a first step of producing an aryl formate and an aromatic carboxylic acid by oxidizing an aromatic aldehyde with an oxygen-containing gas to form a reaction product at 10–120° C. in the absence of solvent; and
   a second step of separating the aromatic carboxylic acid, a mixture of the aryl formate and an unreacted aromatic aldehyde and the aryl formate from the reaction product obtained in the first step;
   the mixture of aryl formate and the unreacted aromatic aldehyde separated in the second step being recycled to the first step.

9. A method of producing a phenol compound, comprising:
   a first step of producing an aryl formate and an aromatic carboxylic acid by oxidizing an aromatic aldehyde with an oxygen-containing gas in an organic solvent having substantially no ability of dissolving water to form a reaction product; and
   a second step of decomposing the aryl formate obtained in the first step to the phenol compound.

10. The method according to claim 9, wherein the organic solvent is at least one selected from the group consisting of an aliphatic hydrocarbon, an aromatic hydrocarbon and an alkyl halide.

11. The method according to claim 9, wherein the second step is carried out by thermally decomposing the aryl formate to the phenol compound and carbon monoxide at 110 to 350° C. in liquid phase in the presence of an alkali metal compound.

12. The method according to claim 11, wherein the alkali metal compound is at least one compound selected from the group consisting of sodium hydroxide, potassium hydroxide, potassium carbonate, sodium alkylphenolates, potassium alkylphenolates, potassium chloride, sodium formate and potassium formate.

13. The method according to claim 9, wherein the second step is carried out by hydrolyzing the aryl formate to the phenol compound and formic acid at 60 to 300° C.

14. The method according to claim 9, wherein the second step is carried out by decomposing the aryl formate to the phenol compound and an alkali salt of formic acid by an aqueous solution of alkali.

15. The method according to claim 9, wherein the second step is carried out by decomposing the aryl formate to the phenol composition and methyl formate by methanol at 50 to 250° C.

16. A method of producing an aryl formate and an aromatic carboxylic acid, comprising a step of oxidizing an aromatic aldehyde to the aryl formate and the aromatic carboxylic acid with an oxygen-containing gas in an organic solvent having substantially no ability of dissolving water to form a reaction product.

17. A method of producing a phenol compound, comprising:
a first step of reacting an aromatic aldehyde having at least one substituent group, formic acid and an aqueous hydrogen peroxide in the presence of an organic solvent having substantially no ability of dissolving water to thereby produce an aryl formate; and
a second step of hydrolyzing the aryl formate obtained in the first step to the phenol compound, wherein the second step is carried out by thermally decomposing the aryl formate to the phenol compound and carbon monoxide at 110 to 350° C. in liquid phase in the presence of an alkali metal compound.

18. The method according to claim 17, wherein the organic solvent is at least one selected from the group consisting of an aliphatic hydrocarbon, an aromatic hydrocarbon and an alkyl halide.

19. The method according to claim 17, wherein the alkali metal compound is at least one compound selected from the group consisting of sodium hydroxide, potassium hydroxide, potassium carbonate, sodium alkylphenolates, potassium alkylphenolates, potassium chloride, sodium formate and potassium formate.

20. A method of producing a phenol compound comprising a step of thermally decomposing an aryl formate to the phenol compound and carbon monoxide in liquid phase in the presence of an alkali metal compound.

21. The method according to claim 20, wherein the alkali metal compound is at least one compound selected from the group consisting of sodium hydroxide, potassium hydroxide, potassium carbonate, sodium alkylphenolates, potassium alkylphenolates, potassium chloride, sodium formate and potassium formate.

* * * * *